United States Patent [19]

Robin et al.

[11] Patent Number: 4,873,349

[45] Date of Patent: Oct. 10, 1989

[54] RUTHENIUM CATALYST FOR BIARYLIC COUPLING; NEW STEGANOLIDES

[75] Inventors: Jean-Pierre Robin; Yannick Landais, both of Le Mans, France

[73] Assignee: Universite Du Maine (Le Mans), Le Mans Cedex, France

[21] Appl. No.: 127,898

[22] PCT Filed: Mar. 5, 1987

[86] PCT No.: PCT/FR87/00055

§ 371 Date: Nov. 5, 1987

§ 102(e) Date: Nov. 5, 1987

[87] PCT Pub. No.: WO87/05289

PCT Pub. Date: Sep. 11, 1987

[30] Foreign Application Priority Data

Mar. 6, 1986 [FR] France .................. 86 03152

[51] Int. Cl.$^4$ ............................ C07D 307/93
[52] U.S. Cl. ..................... 549/298; 540/479; 546/58; 546/75; 546/149; 556/136; 568/633; 585/360; 585/361
[58] Field of Search ............. 549/298; 568/633; 585/360, 361; 556/136; 546/76, 139, 58, 75, 149; 540/450, 479

[56] References Cited

FOREIGN PATENT DOCUMENTS 0141575 8/1984 Japan .................... 549/298

OTHER PUBLICATIONS

Taafrout et al., Tetrahedron Letters, vol. 24, No. 29, 1983, "Neoisostegane, A New Bisbenzocyclooctadienol Actonic Lignand from *Steganotaenia araliacea* Hochst", pp. 2983–2986.

Hicks et al, Tetrahedron Letters, vol. 24, No. 29, 1983, "Neoisostegane, A New Bisbenzocyclooctadiene Lignan Lactone from *Steganotaenia araliacea* Hochst", pp. 2987–2990.

McKillop et al., Journal of Organic Chemistry, vol. 42, No. 4, 1977, pp. 764–765.

Chemical Abstracts, vol. 71, No. 4, Abstract No. 21783p, Jul. 28, 1969, pp. 288–289.

Primary Examiner—Richard A. Schwartz
Assistant Examiner—Zinna Northington
Attorney, Agent, or Firm—Blakely, Sokoloff, Taylor & Zafman

[57] ABSTRACT

A method for forming bridged biaryl compounds via the intramolecular oxidative biarylic coupling of precursor compounds containing two aromatic rings linked via a hydrocarbon chain is disclosed along with the ruthenium catalyst for its implementation and new compounds resulting therefrom. The biarylic coupling method is characterized in that the biarylic precursors are cyclized in the presence of the catalyst tetrakis(trifluoroacetate) of ruthenium (IV).

15 Claims, No Drawings

RUTHENIUM CATALYST FOR BIARYLIC COUPLING; NEW STEGANOLIDES

The present invention relates to a method for the intramolecular oxidative biaryl coupling of precursor compounds containing two aromatic rings linked to each other via a hydrocarbon chain.

The invention also relates to a new organometallic catalyst for oxidative biaryl coupling and to new compounds having bridged biaryl structure, which could be produced by implementing the method of the invention.

A number of bridged biaryl alkaloids have already been synthesized by oxidative biaryl coupling. Thus, S. M. Kupchan et al. have used vanadium oxyfluoride as coupling agent [S. M. Kupchan, K. K. Chakravarti, M. Yokoryama, *J. Pharm. Sci.*, 985 (1963); S. M. Kupchan, A. J. Liepa, V. Kamesvaran, R. F. Bryan, *J. Am. Chem. Soc.*, 6861 (1973) and the references cited; S. M. Kupchan, O. P. Dhingra, C. K. Kim, V. Kamesvaran, *J. Org. Chem.*, 252 (1978) and the references cited; S. M. Kupchan, C. K. Kim, *J. Am. Chem. Soc.*, 5663 (1975) and the references cited].

Additionally, thallium (III) tris(trifluoroacetate) has also already been recommended a coupling agent, for example by A. McKillop et al. [A. McKillop, A. G. Turrell, E. C. Taylor, *J. Org. Chem.*, 765 (1977)] and by Cambie et al. [R. C. Cambie, G. R. Clark, P. A. Craw, P. S. Rutledge, P. D. Woodgate, *Aust. J. Chem.*, 1775 (1984)].

However, these previous techniques have a number of disadvantages. First of all, they do not enable clean reaction mixtures to be obtained at the end of the procedure; it is therefore not easy to separate therefrom the synthesized compound which can therefore be obtained only with very low yields. Furthermore, it should be added that the handling of thallium salts requires very high precautions and that their recovery from the reaction medium presents great practical problems.

Because of these major disadvantages, the scaling up of such synthetic methods to an industrial scale cannot be envisaged. Finally, it should be added that these synthetic methods of the prior art could only be implemented at temperatures well below 0° C., which forms an obvious additional disadvantage.

The present invention is precisely aimed at overcoming all the disadvantages attached to the synthetic method of the known prior art.

The present invention relates to a method for the intramolecular oxidative biaryl coupling of precursor compounds containing two aromatic rings, which may be polycondensed and which may contain one or more hetero atoms such as oxygen or nitrogen, linked to each other via a straight-chain or branched, saturated or unsaturated hydrocarbon chain, which may optionally contain one or more hetero atoms such as oxygen and/or nitrogen, wherein the biaryl precursors are cyclized in the presence of ruthenium (IV) tetrakis(trifluoroacetate), especially produced in situ.

The invention also relates to new ruthenium (IV) tetrakis (trifluoroacetate) catalysts for intramolecular oxidative biaryl coupling.

Finally, the present invention also extends to new biaryl compounds which could be synthesized by implementing the coupling method according to the invention and which prove to have very useful antiviral properties, especially against herpesvirus. These new compounds may also form part of the composition of therapeutic preparations, especially of preparations for use by local application.

Other characteristics and advantages of the present invention will appear on reading the detailed description given below, especially referring to the particular examples of preparation given simply by way of illustration.

In a very general way, the process according to the invention relates to intramolecular oxidative biaryl coupling leading to compounds having a bridged biaryl structure, which are very diverse in nature. This coupling is carried out on precursors containing two aromatic rings linked to each other via a hydrocarbon chain. Each of the two aromatic rings, necessarily present in the structure of the precursors, may be either monocyclic or polycyclic; it may also contain one or more substituents and may contain one or more hetero atoms such as oxygen and/or nitrogen.

The hydrocarbon chain which links the two aromatic rings is straight-chain or branched and may also contain one or more hetero atoms such as oxygen and/or nitrogen.

In general, the coupling according to the invention may be represented in a highly diagrammatic way as follows:

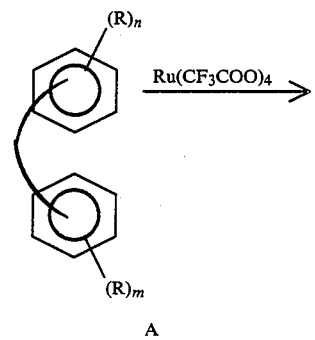

A

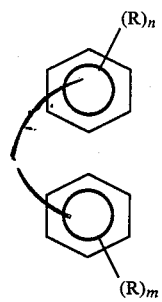

B

In formulae A and B above, the radicals R denote substituents of very diverse nature, especially alkyl or (lower)alkoxy radicals, for example methoxy radicals which may be present to the extent of 3 substituents per ring. In the para position relative to the coupling position, the radicals R may also denote hydroxy groups. In this case, the phenolic coupling using ruthenium (IV) tetrakis(trifluoroacetate) is achieved under excellent conditions.

A relatively large number of categories of natural substances with a high pharmacological value, especially in the field of antitumor agents, have the bridged biaryl structure mentioned above. A number of examples of such compounds are mentioned below simply by way of illustration. They were chosen both for their representativeness as the main compound in the category and for their pharmacological value. All of them can be prepared starting with the corresponding open precursors by implementing the method according to the invention.

| Name and general formula for the family of bridged biaryl compounds | Particular representative of the bridged biaryl family of compounds |
|---|---|
| C bisbenzocyclooctadienelactone lignans | 1 R = H steganolide A<br>2 R = OMe neoisostegane |
| D bisbenzocyclooctadiene lignans | 3 deoxyschizandrine |
| E tetrahydrophenanthrenes | 4 R = H juncusol |
| F aporphine alkaloids | 5 R = Me glaucine<br>6 thalicarpine |

| -continued | |
|---|---|
| Name and general formula for the family of bridged biaryl compounds | Particular representative of the bridged biaryl family of compounds |
| 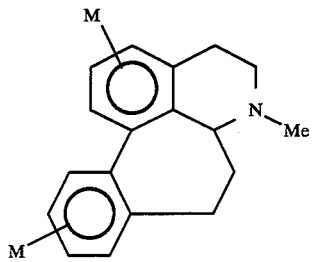<br>G<br>homoaporphine alkaloids | 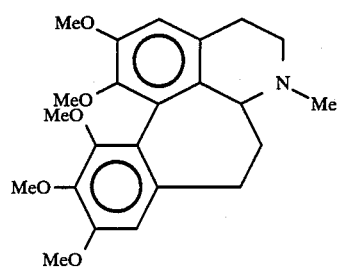<br>7 |
| 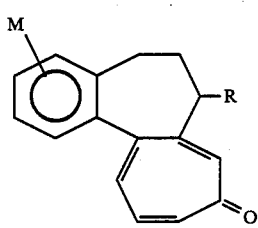<br>H<br>alkaloids of the colchicine group | 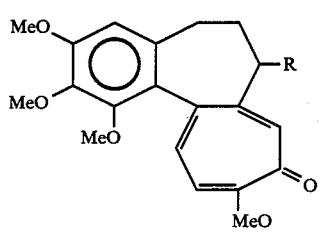<br>8 R= NHAc N—acetylcolchicine |
| 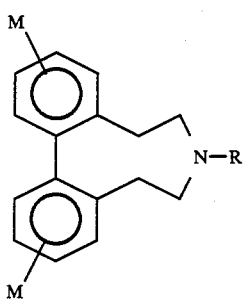<br>I<br>alkaloids of the dibenza-zonine group | 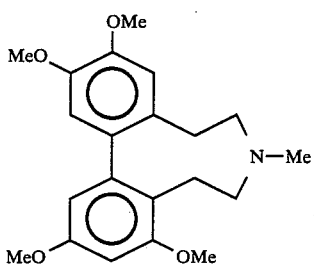<br>9 protostephanine |
| 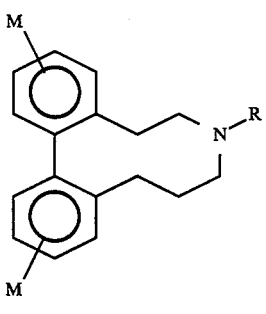<br>J<br>alkaloids of the dibenza-zecine group | 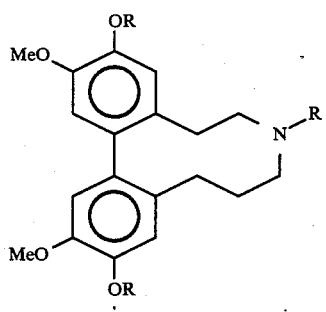<br>10 R = Me |

| Name and general formula for the family of bridged biaryl compounds | Particular representative of the bridged biaryl family of compounds |
|---|---|
| 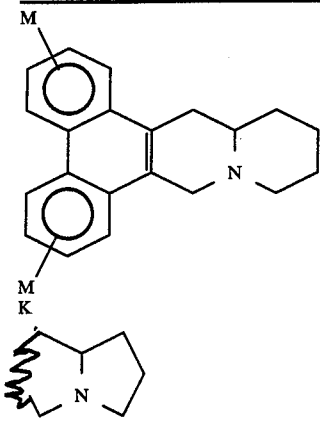<br>M<br>K<br>alkaloids of the phenanthro-quinolizidine (K) and phenanthroindolizidine (L) group | 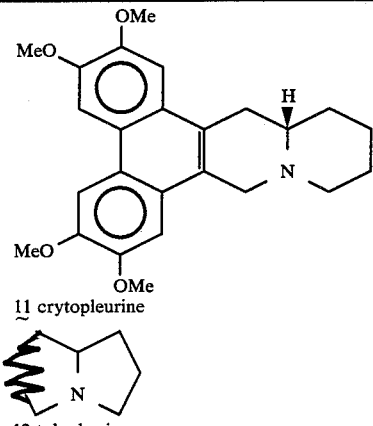<br>11 crytopleurine<br>12 tylophorine |

Some general principles of the coupling reaction according to the invention will be mentioned below, as related to the synthesis of the different types of derivatives having bridged biaryl structure, mentioned in the table above.

Synthesis if bisbenzocyclooctadiene lignans

The lignans 1 to 3 were synthesized using the corresponding dibenzylbutanolide precursors. In the examples given, the yields obtained for the compounds 1 R=H (neoisostegane), 2 R=OMe (steganolide A) and 3 (deoxyschizandrine) are almost quantitative (95 to 100%). The dibenzylbutanolide precursors were prepared by an improvement of the processes of the prior art [E. Brown, J. P. Robin and R. Dhal, J.C.S. Chem. Comm., 556 (1978); M. Taafrout, F. Rouessac and J-P. Robin, Tetrahedron Letters, 3237 (1983)] using the following reaction sequence: the corresponding Stobbe half-ester was selectively reduced using lanthanum borohydride in an ethanolic medium to give, after acidification, the corresponding lactones. The saturated derivatives were obtained by catalytic hydrogenation (hydrogen, Pd-C), either at the half-ester or the lactone stage. These saturated lactones were then alkylated with the aid of appropriate substituted benzyl bromides, using either lithium diisopropyl amide or lithium hexamethyldisilazide as base in tetrahydrofuran, at −80° C., in order to produce the anion. The latter base proved to be particularly effective because some dibenzylbutanolides were obtained with a quantitative yeild. The precursor of deoxyschizandrine 3 was obtained by reducing the lactone (LAH) via the bistosylate of the corresponding primary diol to give the dimethylated derivative, which is an open lignan (diarylbutane category). The biaryl coupling was then performed according to the general procedure described later. The passage to lignans having the so-called normal biaryl linkage followed by the introduction of the benzyl functional group and glycosilation were carried out according to the prior art [T. T. Ishiguro, H. Mizuguchi, K. Tomioka, K. Koga, Chem. Pharm. Bull, 33 (2) 609 (1985); N. Houlbert, E. Brown, J-P. Robin, J. Nat. Prod., 48, 345 (1985)]. With the corresponding cyclic acetals, antiviral properties against the herpesvirus which are as significant as those for reference compounds (Acyclovir) were demonstrated. Like podophyllin these compounds may form part of the composition of medicaments for local use (ointment and eye lotion).

Synthesis of aporphine alkaloids

The open precursor of aporphine alkaloids (general formula F) of 5 R=Me is available on the market (laudanosine). It was subjected to the general coupling reaction forming the subject of the invention to give glaucine 5 R=Me with a yield of analytically pure compound of 92%. A number of analogs of thalicarpine 6 were also synthesized.

Synthesis of homoaporphine alkaloids

Homoaporphine group of alkaloids (general formula G) were obtained by the same method; the benzylethylisoquinoline precursor of 7 was obtained by techniques described in the prior art [S. M. Kupchan, O. P. Dhingra, C. K. Kim, V. Kamesvaran, J. Org. Chem., 252 (1978) and the references cited]. The coupling carried out using Ru(IV) catalyst gave a yield of 87%.

General procedure for biaryl coupling

The general procedure described below can be applies especially to all compounds corresponding to the general formula A. It employs commercial ruthenium oxide as precursor and boron trifluoride etherate as the reagent providing electrophilic assitance. The organometallic salts, which are genuine reagents, were obtained by attacking the oxide with trifluoro acetic acid, in the presence of trifluoro acetic anhydride. The salts were not isolated; however, by analogy with the investigations cited for other metal salts, for example those derived from thallium(III) [R. C. Cambie, G. R. Clark, P. A. Craw, R. S. Rutledge, P. D. Woodgate, Aust. J. Chem., 1775 (1984)], it may be assumed that the reagents produced in situ are indeed trifluoroacetates, and these reagents must be produced as the reaction progresses.

The reaction mixture generally retains a two-phase appearance. Subsequently, the addition of the solvent, followed by the simultaneous addition of boron trifluoride etherate and the precursor to be cyclized, gives to the reaction medium a uniform color ranging from orange yellow to green which proves the presence of radical ions. Control trials carried out without metal oxide left the starting compound unchanged.

Example 7, detailed below, describes the production in situ of ruthenium(IV) tetrakis(trifluoroacetate). The reaction is typically carried out in solvents such as acetonitrile or chlorinated hydrocarbon solvents, for example tetrachloromethane or dichloromethane, depending on the solubility of the starting compounds; however, the latter solvent gave the best results. The reactions are preferably carried out in an inert atmosphere, with stirring, at laboratory temperature. Under these conditions, the reaction rate is slow (6 h to 24 h). In contrast to the results described for thallium, the reaction mixtures obtained at the end of the operation are always very clean; a simple filtration enables the degraded catalyst remaining in suspension to be recovered. A standard washing of the organic phase gives pale yellow solutions from which very pure crude products can be obtained without chromatography. Thus, neoisostegane 2 and steganolide A 1 crystallized spontaneously when the crude reaction mixture was evaporated.

Thus, the use of ruthenium (IV) derivatives in the biaryl oxidative coupling reactions studied has enabled yields higher than those for the best reagents known [vanadium oxyfluoride and thallium tris(trifluoroacetate)] to be obtained. When the coupling reaction is carried out in the presence of ultrasonics, the quantity of catalyst employed is less and/or the reaction time is shortened.

It should be added that in contrast to thallium salts, the harmlessness of ruthenium salts enables the operation to be carried out without any particular precaution and an easy recovery to be achieved. Thus, the salts obtained may be reoxidized by sodium metaperiodate to produce $RuO_4$, very useful reagent in organic synthesis (which itself can be recycled). Additionally, these coupling reactions are carried out at ambient temperature without energy input. The technological equipment to be employed in the case of a large-scale operation is not sophisticated.

Comments on ruthenium(IV) and its derivatives:

There are two types of ruthenium dioxide on the market. The soluble hydrated form gives significantly better results than the insoluble form which, however, can still be employed in these coupling reactions, but with prolonged reaction times.

It should also be mentioned that depending on the degree of hydration of $RuO_2$, the catalyst according to the invention will be employed at a rate of 1 to 5 molar equivalents of $RuO_2$ per mole of biaryl precursor to be cyclized.

So as to make the synthetic method according to the invention understood better, the general reaction scheme for the preparation of bisbenzocyclooctadiene lignans will be given below, followed by some specific examples of implementing the coupling method according to the invention.

REACTION SCHEME FOR THE PREPARATION OF
BISBENZOCYCLOOCTADIENE-LACTONE LIGNANS

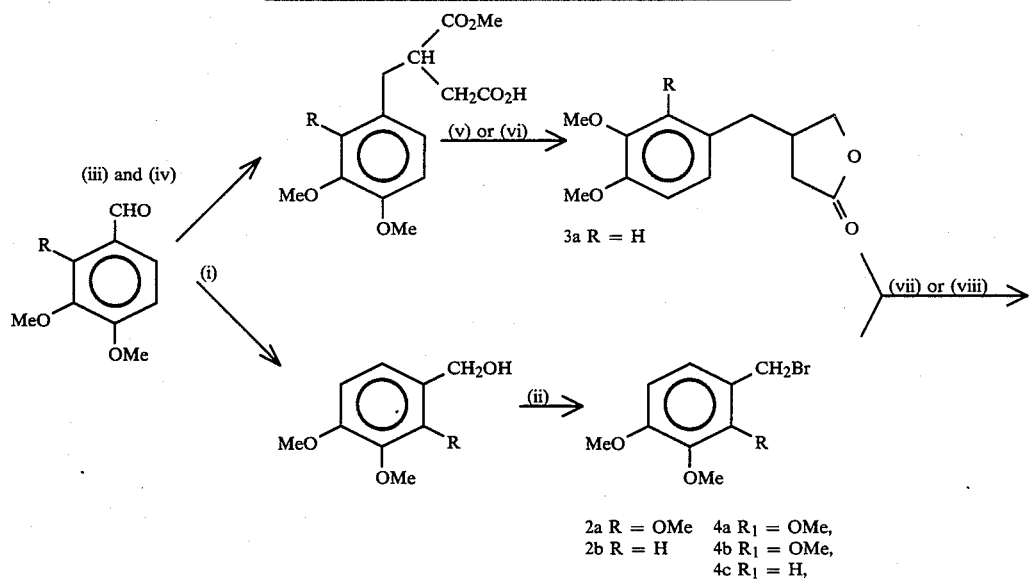

2a R = OMe    4a $R_1$ = OMe,
2b R = H      4b $R_1$ = OMe,
              4c $R_1$ = H,

-continued
REACTION SCHEME FOR THE PREPARATION OF BISBENZOCYCLOOCTADIENE-LACTONE LIGNANS

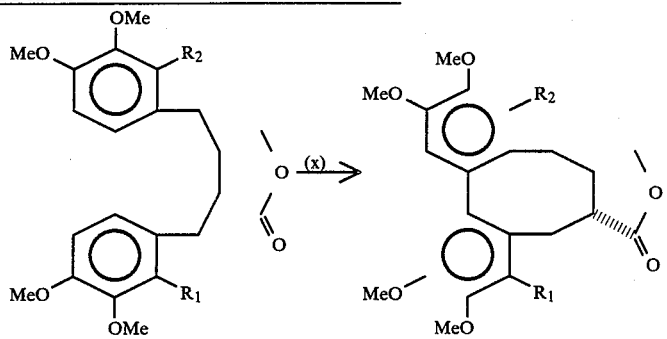

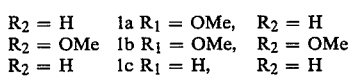

| | | |
|---|---|---|
| R₂ = H | 1a R₁ = OMe, | R₂ = H |
| R₂ = OMe | 1b R₁ = OMe, | R₂ = OMe |
| R₂ = H | 1c R₁ = H, | R₂ = H |

EXPERIMENTAL CONDITIONS
(i) NaBH₄/MeOH—CH₂Cl₂, 0° C., 5 min.; NH₄Cl
(ii) PBr₃/Ether-Pyridine, reflux, 2h
(iii) (CH₂CO₂Me)₂, MeONa/MeOH, −10° C., 3h; HCl
(iv) H₂—Pd—C/AcOEt, 20° C., 6h
(v) KOH, CaCl₂—NaBH₄/EtOH, 0° C., 6h; HCl 6N, 20° C., 30 min.
(vi) KOH, LaCl₃—NaBH₄/EtOH, −40° C., 5 min.; HCl 6N, 20° C., 30 min.
(vii) LiN(iPr)₂/THF—HMPT, −80° C., 3h; HCl 6N, −30° C.
(viii) LiN[Si(CH₃)₃]THF/HMPT, −80° C., 30 min.; HCl 6N, −30° C.
(x) RuO₂, CF₃CO₂H—(CF₃CO)₂O—BF₃OEt₂/CH₂Cl₂, 20° C., 12 to 48 h.

EXAMPLE 1

Preparation of 1-hydroxymethyl-2,3,4-trimethoxybenzene 2 g of commercials 2,3,4-trimethoxybenzaldehyde are placed in a 100 ml three-necked flask equipped with a magnetic stirrer, a gas inlet and a thermometer and are dissolved in 15 ml of CH₂Cl₂+5 ml of ethanol. 200 mg of NaBH₄ (6 mmoles) are added in small portions, at ambient temperature. The contents are stirred for 30 minutes at ambient temperature. TLC (cyclohexane:AcOEt 6:4) indicates a single-spot product. The ethanol is evaporated off and the residue is taken up with ChCl₃, the organic phases are washed with NaCl and then with H₂O, dried over MgSO₄ and evaporated. An analytically pure pale yellow oil is obtained (Y=98%).

EXAMPLE 2

Preparation of 2,3,4-trimethoxybenzyl bromide

A solution of 1-hydroxymethyl-2,3,4-trimethoxybenzene (1 g, 5 mmoles) in anhydrous ethered solution (10 ml) is injected into a three-necked flask supplied with a septum and equipped with a magnetic stirrer, which is swept with argon. Phosphorus tribromide at −20° C. (1.46 g, 5 mmoles) dissolved in ether (8 ml) is then added. The mixture is stirred at −10° C. for 2 hours and then washed with ice-cold water and finally with NaCl, and then dried over MgSO₄. Evaporation at 0° C. under reduced pressure gives a colorless oil (1.24 g) which is homogeneous in TLC (Y=95%).

EXAMPLE 3

Preparation of 2-(2,3,4-trimethoxybenzyl)-3-(3,4-dimethoxybenzyl)-4-butanolide THF freshly distilled over Na (3 ml) and 1.6 ml of 1.6M BuLi (2.54 mmoles) are introduced into a three-necked flask which is flame-dried and equipped with a magnetic stirrer, a gas inlet and a septum. The contents are cooled to −80° C. and freshly distilled diisopropylamine (0.41 ml) is added dropwise. The temperature is increased to −20° C. for 20 minutes and then lowered to −80° C. and a solution of veratryl lactone (500 mg, 2.11 mmoles) in THF (4 ml) is added very slowly, dropwise. Stirring is maintained for 1 hour at −80° C. and the temperature is then increased to −40° C. for 15 minutes and reduced again to −80° C. 0.551 g of 2,3,4-trimethoxybenzyl bromide (2.11 mmoles) dissolved in anhydrous tetrafuran (2.5 ml) containing one equivalent of hexamethylphosphoramide (0.37 ml) is then added very slowly, at −80° C. The temperature is allowed to rise gradually overnight, the mixture is cooled, neutralized (NH₄Cl), the organic phase is washed with brine and then dried (MgSO₄). After evaporation and chromatography of the mixture on silica (toluene:AcOEt 94:6), dibenzylbutanolide is recovered in the form of a thick oil which, after trituration in a dichloromethane-petroleum spirit mixture, yields translucent crystals m.p.=113.5°–114.5° C.(Y=74%).

EXAMPLE 4

Preparation of neoisostegane 192 mg (1.44 mmole) of hydrated ruthenium oxide (soluble form) suspended in 12 ml of dichloromethane are placed in a 100 ml three-necked flask equipped with a magnetic stirrer, which is swept with argon. 1.5 ml (19 mmoles) of trifluoro acetic acid and 0.8 ml (5.7 mmoles) of trifluoro acetic anhydride are added at ambient temperature. 100 mg (0.24 mmole) of 2-(2,3,4-trimethoxybenzyl)-3-(3,4-dimethoxybenzyl)-4-butanolide dissolved in 8 ml of anhydrous dichloromethane, immediately followed by boron trifluoride etherate (0.2 ml, 1.6 mmole) are added, at ambient temperature, to the suspension which is vigorously stirred. After a few minutes, the supernatant of the solution becomes pale yellow in color. The suspension is thus maintained stirred at ambient temperature overnight, at the end of which time, monitoring by thin layer chromatography indicates the presence of a single product, with the complete disappearance of the starting product. The reaction mixture is treated with NaHCO$_3$ and then filtered through filter paper in order to remove the solid products. The organic phase is then decanted and the aqueous phase extracted with ethyl acetate. The organic phases are then combined, dried over MgSO$_4$ and evaporated to give a pale yellow solio which is chromatographically pure. After filtering through silica (dichloromethane), a white solid (m=98 mg, Yield: 98%) is obtained, which is comparable in all respects (chromatography, IR spectroscopy and $^1$H NMR spectroscopy) to the compound obtained from the plant species *Steganotaenia araliacea* Hochst (Umbelliferae), by high resolution analytical liquid chromatography of an ethanolic extract.

EXAMPLE 5

Preparation of methyl 2,3,4-trimethoxybenzylidene hemisuccinate 2.8 g (0.12 mole) of freshly cut sodium is placed in a 250 ml three-necked flask equipped with a magnetic stirrer, a thermometer, a gas inlet and a condenser and 40 ml of methanol dissolved over magnesium are then added dropwise. Stirring is maintained during the addition of MeOH and the mixture is heated to reflux in order to complete the dissolution of Na. When the latter is completely dissolved, the major portion of methanol is distilled and a hot mixture of commercial 2,3,4-trimethoxybenzaldehyde (15 g, 0.076 mole) and dimethyl succinate (16 g, 0.106 mole) is then added quickly. The reaction mixture is heated under reflux for 5 hours and then, after cooling, acidified with 10% HCl (cooled to −20° C.). The organic phase is decanted and the aqueous phase extracted with dichloromethane. The organic phases collected are dried (MgSO$_4$) and evaporated under reduced pressure. After trituration in ether, the oil obtained yeilds pale yellow crystals m.p.=104°-105° C. (ether).

EXAMPLE 6

Preparation of methyl 2,3,4-trimethoxybenzyl hemisuccinate 20 g (0.08 mole) of crude methyl 2,3,4-trimethoxybenzylidene hemisuccinate (Example 5) dissolved in a 1:1 AcOH/AcOEt mixture (100 ml) are placed in a hydrogenation vessel and palladinized charcoal with a 10% palladium content (2 g) is added to it. The hydrogenation vessel is placed in a Parr bomb (344.75×10$^3$ Pa), and the stirring is continued for 10 hours at ambient temperature. After filtering twice through filter paper and removing the solvent under reduced pressure, the crude saturated half-ester is collected in the form of a white solid (Yield: 97%).

EXAMPLE 7

Preparation of 2,3,4-trimethoxy-2-benzyl-4-butanolide 13.0 g (42 mmoles) of methyl 2,3,4-trimethoxybenzyl hemisuccinate (Example 6) are dissolved in 400 ml of absolute ethanol in a three-necked flask equipped with a magnetic stirrer, a gas inlet, a thermometer and a dropping funnel. 2.35 g of KOH pellets (42 mmoles) are added and when they are dissolved completely, lanthanum chloride powder (LaCl$_3$) (10.3 g, 42 mmoles) is added. The mixture which is vigorously stirred is cooled to −40° C. and sodium borohydride (1.4 g, 32 mmoles) dissolved in ethanol cooled to 0° C. is then added dropwise, with care (the addition is accompanied by a violet gas evolution). As soon as the addition is complete, the mixture is acidified, in the cold state, with 50% HCl and stirred for 1 hour at 20° C. Ethanol is then evaporated off and the aqueous phase is extracted with dichloromethane. The organic phases are washed, dried and then evaporated. A pale yellow fluid oil is collected (9.83 g, Yield=88%) which, on triturating in ether, gives a crystalline cake m.p.=59.5°-60.5 (ether); IR spectrum (nujol): 1778 (CO lactone), 1601 (C=C), 1263 NMR spectrum (CDCl$_3$): 2.07 to 3.07 ppm (m, 5H) aliphatic; 3.81 ppm (s, 3H) CH$_3$O; 3.87 to 4.5 ppm (m, 2H) aliphatic H; 6.73 to 7.11 ppm (m, 3H) aromatic H; 7.18 to 7.5 ppm (m, 1H) aromatic H.

EXAMPLE 8

Preparation of 2,3-bis(2,3,4-trimethioxybenzyl)-4-butanolide

THF freshly distilled over Na (30 ml) and 16 ml of 1.6M BuLi (25.4 mmoles) are introduced into a three-necked flask which is flame-dried and equipped with a magnetic stirrer, a gas inlet and a septum, the contents are then cooled to −80° C. and 1 equivalent of dry hexamethyldisilazane is quickly added. The temperature is then increased to −40° C. for 1 minute and then reduced to −80° C. and 2,3,4-trimethoxy-2-benzyl-4-butanolide (5.85 g, 22 mmoles) in 20 ml of anhydrous THF (dibenzylbutanolide from Example 7) is added dropwise. Stirring is maintained for 1 hour at −80° C. and the temperature is then increased to −40° C. for 15 minutes and reduced again to −80° C. 5.74 g (22 mmoles) of 2,3,4-trimethoxybenzyl bromide (Example 2) dissolved in anhydrous tetrahydrofuran (15 ml) containing one equivalent of hexamethylphosphoramide (3.5 ml) are added. The temperature is allowed to rise gradually to −30° C. and the mixture is neutralized with diluted HCl. The organic phase is washed with brine and then dried over MgSO$_4$. After evaporation and chromatography of the mixture on silica (toluene-AcOEt), 8.33 g of dibenzylbutanolide are collected in the form of a colorless glass which is homogeneous in TLC (Yield=91%), which, on dissolving in ether, yields fine white crystals m.p.=87°-88° C.; IR spectrum (nujol): 1772, 1601 cm$^{-1}$; $^1$H NMR spectrum (CDCl$_3$): 2.2 to 3.5 (6H, m) aliphatic H; 3.81 (3H, s) OMe; 3.85 (6H, s) OMe×2; 3.90 (3H, s) OMe; 3.92 (3H, s) OMe; 3.94 (3H, s) OMe; 4.0 to 4.5 (2H, m) —CH$_2$OCO—; 6.53 to 7.11 (4H, m) aromatic H.

EXAMPLE 9

Preparation of steganolide A 72 mg (0.54 mmole) of hydrated RuO$_2$ (soluble form) suspended in 12 ml of dichloromethane are placed in a three-necked flask equipped with a magnetic stirrer, which is swept with argon. 0.7 ml (9 mmoles) of trifluoro acetic acid (TFA) and 0.4 ml of trifluoro acetic anhydride are added at ambient temperature. 40 mg (0.09 mmole) of 2,3-bis(2,3,4-trimethoxybenzyl)-4-butanolide dissolved in 8 ml of anhydrous dichloromethane are then added to the suspension at ambient temperature, immediately followed by the addition of boron trifluoride etherate (0.1 ml, 0.8 mmole). After standing overnight at ambient temperature, monitoring by thin layer chromatography indicates a single product. The reaction mixture is treated as in Example 4. After concentrating under reduced pressure and dissolving in the heated state in a dichloromethane-ether mixture, the yellow oil obtained yields, on cooling, steganolide A in the racemic form, in the form of fine translucent prisms m.p.=173°–175° C. (Yield=94%). This synthetic steganolide A proved comparable in all respects to the compound of natural origin (see Example 11 below).

MS: M+ =444.1791 ($C_{24}H_{28}O_8$); IR spectrum ($CHCl_3$) 1776 cm$^{-1}$; $^1$H NMR spectrum 500 MHz ($CDCl_3$) (ppm): 6.52 (2H, s) H-1 and H-12; 4.39 (1H, dd, $J_{13a\text{-}13b}$=8.3 Hz, $J_{13a\text{-}6}$=6.7 Hz) H-13a; 3.95 (3H, s); 3.93 (3H, s); 3.92 (3H, s) and 3.86 (6H, s) OMe-2, OMe-3, OMe-4, OMe-9, OMe-10 and OMe-11; 3.79 (1H, dd, $J_{13a\text{-}13b}$=8.3 Hz; $J_{13b\text{-}6}$=11.0 Hz) H-13b; 3.66 (1H, d, $J_{8b\text{-}8a}$=13.2 Hz) H-8b; 3.14 (1H, d, $J_{5a\text{-}5b}$=12.9 Hz) H-5a; 2.08 (1H, m) H-6; 2.01 (1H, dd, $J_{7\text{-}8a}$=9.0 Hz, $J_{7\text{-}6}$=13.4 Hz) H-7; 1.97 (1H, dd, $J_{5b\text{-}6}$=9.5 Hz, $J_{5a\text{-}5b}$=12.9 Hz) H-5b; 1.91 (1H, dd, $J_{8a\text{-}8b}$=13.2 Hz, $J_{8a\text{-}7}$=9.0 Hz) H-8a.

EXAMPLE 10

Thermal atropoisomerization of steganolide A

A closed tube equipped with a valve is swept with argon for 10 minutes and 20 mg of a steganolide A mixture are placed therein. The compound, maintained under slight excess pressure of argon, is then heated in a metal bath for 2 hours at 220° C. After cooling, the brown oil obtained is taken up directly with $CDCl_3$ with a view to carrying out NMR spectroscopy at 90 MHz. The spread of the spectrum over 5 ppm in the aromatic region and enlargement of the peaks enables the ratio of the two atropoisomers iso:normal to be determined by integration (85:15).

EXAMPLE 11

Isolation of steganolide A from Steganotaenia araliacea

Detailed high resolution analytical liquid chromatographic studies (Li-chrocart, Lichrospher CH-8/2 Merck, 5μ, 250×4 mm, 1.2 ml/min., 28×10$^6$ Pa, ternary gradient $H_2O$:MeOH:$CH_3CN$) on an active fraction of the ethanolic extract of a sample of Steganotaenia araliacea (Umbelliferae) of West African original enabled new compounds present in smaller quantities to be detected.

The isolation of steganolide A will be described below.

High performance preparative chromatography (Hibar RP8 Merck 7μ, 250×25 mm, MeOH:$H_2O$, 12.5 ml/min.), enabled an amorphous compound to be obtained: MS:M+ =444.1791 ($C_{24}H_{28}O_8$); $[\alpha]_D^{20}$ +67.9° (C=1.65; $CHCl_3$); IR spectrum ($CHCl_3$) 1776 cm$^{-1}$; $^1$H NMR spectrum 500 MHz ($CDCl_3$) (δ ppm): 6.52 (2H, s) H-1 and H-12; 4.39 (1H, dd, $J_{13\alpha\text{-}13\beta}$=8.3 Hz, $J_{13\alpha\text{-}6}$=6.7 Hz) H-13α; 3.95 (3H, s); 3.93 (3H, s); 3.92 (3H, s) and 3.86 (6H, s) $OCH_3$-2, $OCH_3$-3, $OCH_3$-4, $OCH_3$-9, $OCH_3$-10 and $OCH_3$-11; 3.79 (1H, dd, $J_{13\alpha\text{-}13\beta}$=8.3 Hz; $J_{13\alpha\text{-}6}$=11.0 Hz) H-13β; 3.66 (1H, d, $J_{8\beta\text{-}8\alpha}$=13.2 Hz) H-8β; 3.14 (1H, d, $J_{5\alpha\text{-}5\beta}$=12.9 Hz) H-5α; 2.08 (1H, m) H-6; 2.01 (1H, dd, $J_{7\text{-}8\alpha}$=9.0 Hz, $J_{7\text{-}6}$=13.4 Hz) H-7; 1.97 (1H, dd, $J_{5\beta\text{-}6}$=9.5 Hz), $J_{5\alpha\text{-}5\beta}$=12.9 Hz) H-5β; 1.91 (1H, dd, $J_{5\alpha\text{-}8\beta}$=13.2 Hz, $J_{8\alpha\text{-}7}$=9.0 Hz) H-8α.

A study of the above spectrum shows that it is a bridged biaryl compound of the bis-benzocyclooctadienelactone type, carrying 6 aromatic methoxyl groups and containing a —$CH_2$— in position with respect to a hetero atom (lactone methylene at 3.79 and 4.39 ppm). The absence of a methoxyl group shifted towards the higher fields proves that the latter are on positions 2, 3, 4, 9, 10 and 11. The whole of the aliphatic skeleton could be determined unambiguously using double irradiation experiments. From the stereochemical point of view, the value 13.4 Hz for the H$_6$–H$_7$ coupling shows the presence of a trans lactone linkage. The observation of H$_{8\beta}$–H$_7$ coupling (J=0 Hz) confirms the iso atropoisomerism whereas the absence of H$_8$–H$_9$ benzyl coupling is an additional argument in favor of the presence of a methoxyl group in position 9. As in the case of neoisostegane, the steric compression between the hydrogen H$_{8\beta}$ and this methoxyl leads to a splitting of the figures for benzyl protons H$_{8\alpha}$ and H$_{8\beta}$, resulting in a difference in chemical shift of 1.75 ppm (as against 1.76 for the latter). In the case of steganolide A, a comparable phenomenon is observed for the other benzyl proton pair H$_{5\alpha}$ and H$_{5\beta}$, this being a difference of 1.17 ppm as against 0.26 ppm for neoisostegane, which is in conformity with the presence of methoxyl on C-4. These spectroscopic values compared with those already obtained for the diastereoisomers of steganes and neoisostegane suggest that this compound is (+)-(M, 6R, 7R)-steganolide A.

EXAMPLE 12

Preparation of glaucine 5 from laudanosine 150 mg (1.12 mmole) of hydrated ruthenium oxide suspended in 18 ml of anhydrous $CH_2Cl_2$ are introduced into a 100 ml three-necked flask equipped with a magnetic stirrer, a gas inlet, a thermometer and a septum and 1.2 ml (16 mmoles) of trifluoro acetic acid and 0.7 ml (4.96 mmoles) of trifluoro acetic anhydride are added. The suspensionis cooled to −10° C. in an ice-acetone bath. 0.1 g (0.28 mmole) of DL-Laudanosine dissolved in 6 ml of anhydrous $CH_2Cl_2$ is added, immediately followed by the addition of 0.16 ml (1.3 mmole) of $BF_3$ etherate. The red solution thus obtained is stirred at ambient temperature for 24 hours, the total disappearance of the starting compound being indicated by TLC ($CH_2Cl_2$:MeOH 9:1). The mixture is treated with 10% $NH_4OH$ to pH 9 and the heterogeneous solution is then filtered through filter paper. The organic phase is decanted and the aqueous phase extracted with AcOEt. The organic phases are washed with saturated NaCl followed by $H_2O$ and then dried over $MgSO_4$. After evaporation, crude glaucine is collected in the form of a brown oil which is homogeneous in TLC (Yield=92%), which, after silica gel chromatography ($CH_2Cl_2$: MeOH 99:1) gives a pale yellow oil which crystallizes (needles) in a $CH_2Cl_2$:ether mixture (m.p.=134°–136° C.) (lit.=137°–139° C.).

EXAMPLE 13

Preparation of analog 1d of formula

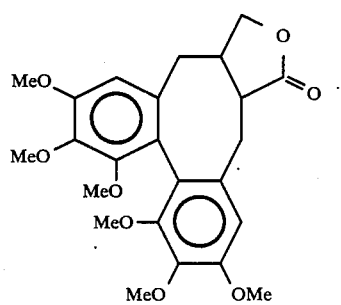

1d 0.060 g (0.448 mmole) of hydrated ruthenium oxide suspended in 10 ml of anhydrous $CH_2Cl_2$ is placed in a 100 ml three-necked flask equipped with a magnetic stirrer, a gas inlet, a septum and a thermometer and 0.48 ml (6.19 mmoles) of trifluoro acetic acid and 0.25 ml (1.78 mmole) of trifluoro acetic anhydride are added. The suspension is cooled to $-10°$ C. using an ice-acetone bath, 0.1 g (0.224 mmole) of 3-(3′,4′,5′-trimethoxybenzyl)-3-(3,4,5-trimethoxybenzyl)-4-butanolide dissolved in 5 ml of anhydrous $CH_2Cl_2$ is then added, immediately followed by the addition of u.u095 ml (0.083 mmole) of $8F_3$ etherate. The mixture is stirred vigorously for 24 hours at ambient temperature. When TLC (toluene:AcOEt 7:3) shows the complete disappearance of the starting compound, the suspension is cooled and treated with 5% $NaHCO_3$, the mixture is filtered and the aqueous phase is extracted with AcOEt. The combined organic phases are washed with saturated NaCl followed by $H_2O$ and then dried over $MgSO_4$ and finally evaporated. A pale yellow oil which is homogeneous in TLC is thus obtained (m=93 mg) (Yield=93%).

EXAMPLE 14

Preparation of analog 1e of formula

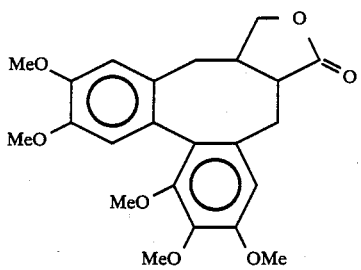

0.064 g (0.480 mmole) of hydrated ruthenium oxide suspended in 10 ml of anhydrous $CH_2Cl_2$ is placed in a 100 ml three-necked flask equipped with a magnetic stirrer, a gas inlet and a thermometer and 0.51 ml (6.62 mmoles) of trifluoro acetic acid and 0.27 ml (1.91 mmole) of trifluoro acetic anhydride are added. The suspension is thus cooled to $-10°$ C. using an ice-acetone bath. 0.1 g (0.24 mmole) of 3-(3′,4′,5′-trimethoxybenzyl)-3-(3,4,-dimethoxybenzyl)-4-butanolide dissolved in 5 ml of anhydrous $CH_2Cl_2$ is then added, immediately followed by the addition of 0.01 ml (0.089 mmole) of $BF_3$ etherate. The mixture is vigorously stirred for 24 hours at ambient temperature. When the complete disappearance of the starting compound is indicated by TLC (toluene:AcOEt 7:3), the mixture is cooled to $-10°$ C. and treated with 5% $NaHCO_3$ and then filtered through the filter paper. The aqueous phase is extracted with AcOEt and the combined organic phases are washed with saturated NaCl followed by $H_2O$ and then dried over $MgSO_4$. After evaporating the solvent, a pale yellow oil is obtained, which crystallizes in a $CH_2Cl_2$:ether mixture, yielding 94 mg (Yield=94%) a solid in the form of needles (m.p.=213°–215° C.).

Comparative study of different oxidative biaryl coupling reaagents

In order to demonstrate the improvements obtained by using the new catalyst forming the subject of the present invention, the results obtained will be given in the table below in comparison with those obtained with other catalysts, in the context of the synthesis of some specific derivatives; for analogs 1a, 1b and 1c, the synthesis scheme may be summarized as follows:

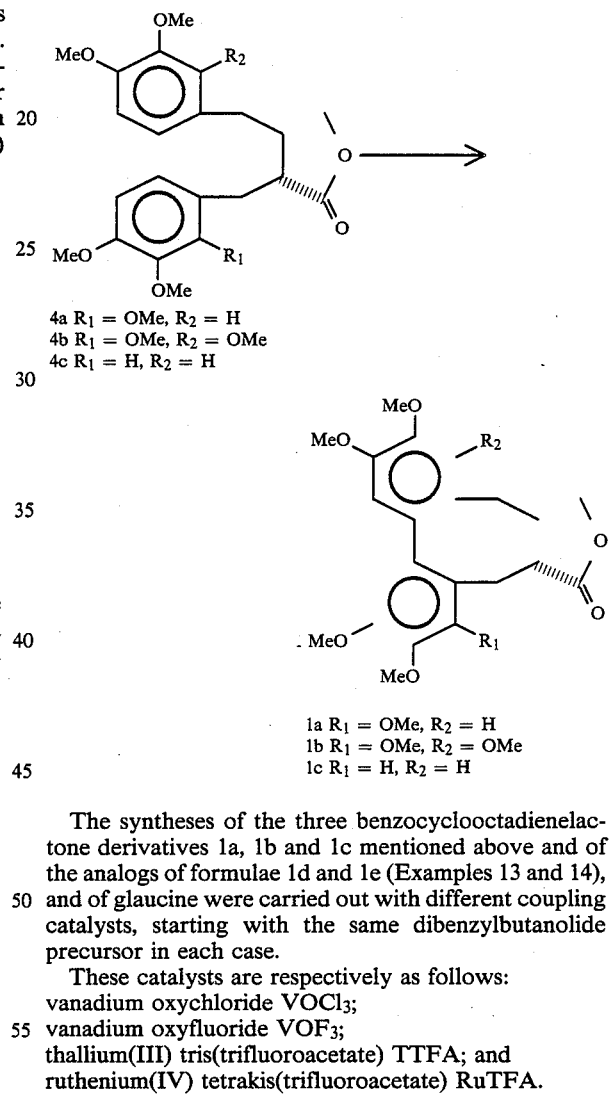

4a $R_1$ = OMe, $R_2$ = H
4b $R_1$ = OMe, $R_2$ = OMe
4c $R_1$ = H, $R_2$ = H

1a $R_1$ = OMe, $R_2$ = H
1b $R_1$ = OMe, $R_2$ = OMe
1c $R_1$ = H, $R_2$ = H

The syntheses of the three benzocyclooctadienelactone derivatives 1a, 1b and 1c mentioned above and of the analogs of formulae 1d and 1e (Examples 13 and 14), and of glaucine were carried out with different coupling catalysts, starting with the same dibenzylbutanolide precursor in each case.

These catalysts are respectively as follows:
vanadium oxychloride $VOCl_3$;
vanadium oxyfluoride $VOF_3$;
thallium(III) tris(trifluoroacetate) TTFA; and
ruthenium(IV) tetrakis(trifluoroacetate) RuTFA.

TABLE OF COMPARATIVE RESULTS

| Compound | Catalyst | Reaction media | t(°C.) | Time (h) | Y(%) |
|---|---|---|---|---|---|
| Neoisostegane 1a | $VOCl_3$ | $CF_3CO_2H$—$(CF_3CO)_2O$—$CH_2Cl_2$ | −80 | 3 | 50[a] |
| " | $VOF_3$ | $CF_3CO_2H$—$(CF_3CO)_2O$—$CH_2Cl_2$ | −50 | 3 | 46[a] |
| " | TTFA | $CF_3CO_2H$—$(CF_3CO)_2O$—$BF_3Et_2O$—$CH_2Cl_2$ | −10 | 2 | 75 |
| " | RuTFA[b] | $CF_3CO_2H$—$(CF_3CO)_2O$—$BF_3Et_2O$—$CH_2Cl_2$ | +20 | 12 | 98 |
| Steganolide A 1b | TTFA | $CF_3CO_2H$—$(CF_3CO)_2O$—$BF_3Et_2O$—$CH_2Cl_2$ | −10 | 1 | 69 |
| " | RuTFA | $CF_3CO_2H$—$(CF_3CO)_2O$—$BF_3Et_2O$—$CH_2Cl_2$ | +20 | 48[c] | 96 |
| Analog 1c | TTFA | $CF_3CO_2H$—$(CF_3CO)_2O$—$BF_3Et_2O$—$CH_2Cl_2$ | −10 | 1 | 79[d] |

-continued

TABLE OF COMPARATIVE RESULTS

| Compound | Catalyst | Reaction media | t(°C.) | Time (h) | Y(%) |
|---|---|---|---|---|---|
| " | RuTFA | $CF_3CO_2H$—$(CF_3CO)_2O$—$BF_3Et_2O$—$CH_2Cl_2$ | +20 | 48 | 97 |
| Analog 1d | TTFA | $CF_3CO_2H$—$(CF_3CO)_2O$—$BF_3Et_2O$—$CH_2Cl_2$ | −10 | 1 | 70 |
| " | RuTFA | $CF_3CO_2H$—$(CF_3CO)_2O$—$BF_3Et_2O$—$CH_2Cl_2$ | +20 | 24 | 93[d] |
| Analog 1e | TTFA | $CF_3CO_2H$—$(CF_3CO)_2O$—$BF_3Et_2O$—$CH_2Cl_2$ | 0 | 3 | 72[d] |
| " | RuTFA | $CF_3CO_2H$—$(CF_3CO)_2O$—$BF_3Et_2O$—$CH_2Cl_2$ | +20 | 24 | 94[d] |
| Glaucine 2b | TTFA | $CF_3CO_2H$—$(CF_3CO)_2O$—$BF_3Et_2O$—$CH_2Cl_2$ | 0 | 3 | 65[d] |
| " | RuTFA | $CF_3CO_2H$—$(CF_3CO)_2O$—$BF_3Et_2O$—$CH_2Cl_2$ | +20 | 24 | 92[d] |

[a]Presence of secondary degradation products
[b]Not isolated, produced in situ with $RuO_2.xH_2O$ (1.5 eq.)
[c]Reaction time increased by a factor of approximately two in the case of the anhydrous form of $RuO_2$
[d]Already described in the prior art R. C. Cambie, G. R. Clark, P. A. Craw P. S. Rutledge The results summarized in the above table demonstrate the significant superiority of the catalyst according to the invention (RuTFA) over other known coupling agents. In contrast to the observations described for known reagents, in the case of RuTFA, the reaction mixtures obtained at the end of the operations are colorless and the excess catalyst may be recovered simply by filtering.

We claim:

1. A method for forming bridged biaryl compounds via the intramolecular biaryl coupling of compounds containing two aromatic rings, which may be polycondensed and which may contain one or more hetero atoms selected from oxygen and nitrogen, linked to each other at the ortho position via a straight-chain to branched, saturated or unsaturated hydrocarbon chain which may optionally contain one or more hetero atoms selected from oxygen and nitrogen, wherein the unbridged biaryl precursors are coupled in the presence of ruthenium (IV) tetrakis (trifluoroacetate) produced in situ by reacting trifluoroacetic acid with ruthenium dioxide $RuO_2$ in the presence of trifluoroacetic anhydride.

2. The method as claimed in claim 1, wherein the reaction of trifluoroacetic acid with ruthenium dioxide is carried out in the presence, in addition, of boron tribluoride etherate $BF_3Et_2O$ to provide elelctrophilic assistance.

3. The method as claimed in claim 2, wherein ruthenium (IV) tetrakis (trifluoroacetate) is employed at a rate of 1 to 10 molar equivalent)s) of ruthenium dioxide $RuO_2$ per mole of biaryl precursors to be cyclized.

4. The method as claimed in one of claims 1, 2 or 3, wherein the cyclization reaction is carried out in an organic solvent which is substantially anhydrous.

5. The method as claimed in one of claims 1, 2 or 3, wherein the cyclization reaction is carried out under an integer gas atmosphere.

6. The method as claimed in one of claims 1, 2 or 3, wherein the cyclization reaction is carried out at a temperature between 0° C. and 25° C.

7. The method as claimed in claim 1, wherein the precursor compound to be cyclized is chosen from amongst open precursors of bisbenzocyclooctadiene lignans, bisbenzocyclooctadiene-lactone lignans, tetrahydrophenanthrenes, aprophine · alkaloids, homoaporphine alkaloids, alcaloids of the colchicine group, alkaloids of the dibenzazonine group, alkaloids of the phenanthroindolizidine group.

8. The method as claimed in one of claims 1 2, or 3 wherein the cyclization reaction is carried out under ultrasonics.

9. The method as claimed in one of claims 1 or 7, wherein the precursor compound to cyclized is 2-(2,3,4-trimethoxybenzyl)-3-(3,4-dimethoxybenzyl)-4-butanolide.

10. The method as in claims in one of claims 1 or 7, wherein the precursor compound to be cyclized is 2,3-bis-(2,3,4-trimethoxybenzyl)-4-butanolide.

11. The compound of formula:

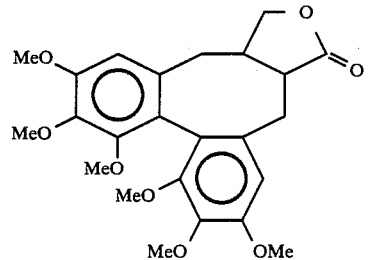

12. Steganolide A of formula:

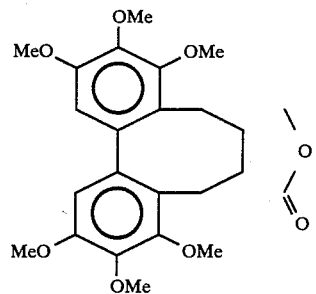

13. The method of claim 1, wherein the cyclization reaction is carried out in a substantially anhydrous chlorinated hydrocarbon solvent.

14. The method of claim 13, wherein the substantially anhydrous hydrocarbon solvent is dichloromethane.

15. The method of claim 14, 1, 2 or 3, wherein the inert gas atmosphere is argon.

* * * * *